(12) United States Patent
Kim et al.

(10) Patent No.: US 7,794,760 B2
(45) Date of Patent: Sep. 14, 2010

(54) **HERBAL MIXTURE EXTRACT OF *PLEUROTUS ERYNGII*, *ACANTHOPANACIS* CORTEX AND *NOTOGINSENG* RADIX AND A COMPOSITION COMPRISING THE SAME FOR PREVENTION AND TREATMENT OF PERIODONTITIS**

(75) Inventors: Jung-Keun Kim, Seongnam-si (KR); Se-Won Kim, Cheonan-si (KR); Hyung-Gun Kim, Seoul (KR); Seon-Yle Ko, Daejeon (KR); Dong-Heon Baek, Seoul (KR)

(73) Assignee: Oscotec Inc., Chungcheongnam-Do (KR)

( * ) Notice: Subject to any disclaimer, the term of this patent is extended or adjusted under 35 U.S.C. 154(b) by 62 days.

(21) Appl. No.: 11/840,894

(22) Filed: Aug. 17, 2007

(65) Prior Publication Data

US 2008/0038212 A1 Feb. 14, 2008
US 2010/0196288 A9 Aug. 5, 2010

Related U.S. Application Data

(63) Continuation of application No. PCT/KR2006/000544, filed on Feb. 17, 2006.

(30) Foreign Application Priority Data

Feb. 18, 2005 (KR) .................. 10-2005-0013702

(51) Int. Cl.
*A61K 36/254* (2006.01)
*A61K 36/258* (2006.01)
*A61K 36/00* (2006.01)

(52) U.S. Cl. ...................... 424/728; 424/725
(58) Field of Classification Search ............ None
See application file for complete search history.

(56) References Cited

U.S. PATENT DOCUMENTS 5,858,735 A * 1/1999 Peng et al. ............ 435/100

FOREIGN PATENT DOCUMENTS

| CN | 1633969 | * | 7/2005 |
| CN | 1660038 | * | 8/2005 |
| JP | 1994-298633 A | | 4/1993 |
| JP | 2000026256 A | * | 1/2000 |
| JP | 2003089641 A | * | 3/2003 |
| KR | 0373498 B1 | | 2/2003 |
| KR | 0399374 B1 | | 10/2003 |
| KR | 2004-0100760 A | | 12/2004 |
| KR | 2005-0110809 A | | 11/2005 |
| KR | 2006-0003942 A | | 1/2006 |

OTHER PUBLICATIONS

Philipson. New Drugs From Nature—It Could Be Yew. Phytotherapy Research. 13, 1999, pp. 2-8.*
Revilla et al.Comparison of Several Procedures Used for the Extraction of Anthocyanins From Red Grapes. J. Agric. Food Chem. 1998, 46, pp. 4592-4597.*
Minkin, C., Calcif, Tissue Int., 34:285-290, 1982.
Kong, Y.Y. et al., Nature 402:304-309, 1999.

* cited by examiner

*Primary Examiner*—Patricia Leith
*Assistant Examiner*—Melenie McCormick
(74) *Attorney, Agent, or Firm*—Lucas & Mercanti, LLP

(57) ABSTRACT

The present invention relates to a herbal mixture extract of *Pleurotus eryngii*, *Acanthopanacis Cortex* and *Notoginseng Radix* and a composition for prevention and treatment of periodontal disease containing the herbal mixture extract as an active ingredient, more precisely, a herbal mixture extract having activities of inhibiting the generation and activation of osteoclasts by enhancing the expression of osteoprotegerin (OPG) in osteoblasts, preventing alveolar bone from destruction by inhibiting the proliferation of osteoclasts and maintaining the growth of periodontal ligament cells and gingival fibroblasts, and a composition for prevention and treatment of periodontal disease containing the above mixture as an active ingredient.

8 Claims, 4 Drawing Sheets

HERBAL MIXTURE EXTRACT OF *PLEUROTUS ERYNGII, ACANTHOPANACIS* CORTEX AND *NOTOGINSENG* RADIX AND A COMPOSITION COMPRISING THE SAME FOR PREVENTION AND TREATMENT OF PERIODONTITIS

CROSS-REFERENCE TO RELATED APPLICATION

This application is a continuation of PCT International Application No. PCT/KR2006/00544, filed Feb. 17, 2006, which claims the benefit of priority from Korean Patent Application No. 10-2005-0013702 filed on Feb. 18, 2005.

TECHNICAL FIELD

The present invention relates to a herbal mixture extract of *Pleurotus eryngii, Acanthopanacis Cortex* and *Notoginseng Radix* and a composition for prevention and treatment of periodontal disease containing the herbal mixture extract as an active ingredient.

BACKGROUND ART

Periodontal tissue is composed of alveolar bone, gingiva and periodontal ligament. Gingiva is a part of dental supporting apparatus in oral cavity, from which disease such as gingivitis is set off. As disease gets serious to spread deep into periodontal supporting apparatus, dental root and periodontal ligament attached on alveolar bone are destroyed, leading to the destruction of alveolar bone itself. As a result, periodontitis is developed.

Periodontal disease including gingivitis and periodontitis is characterized by inflammation in dental supporting apparatus caused by bacterial infection, which carries the symptoms of bleeding, periodontal pocket formation and alveolar bone destruction, leading to the loss of teeth. Periodontal disease progresses by following procedure: bacterial colony formation, invasion of bacteria into periodontal tissue and destruction of periodontal tissue. Particularly, oral bacteria form dental plaque due to poor oral hygiene, resulting in bleeding in gingiva and halitosis due to inflammation. When these symptoms are continued, a gap between teeth and gingiva becomes bigger, resulting in forming periodontal pocket, where bacteria causing periodontal diseases proliferate, resulting in periodontitis. As periodontitis progresses, gingival bleeding can be triggered by even weak stimulus such as tooth-brushing and becomes swollen, and sometimes it progresses to acute inflammation carrying great pain. The inflammation reduces the function of osteoblasts to form the bone with collagen, calcium and hydroxyapatite of phosphorus and increases the function of osteoclasts to destroy and resorb bone. As a result, alveolar bones are decreased in amount and further destroyed, leading to the loss of teeth. Osteoclasts are derived from monocytes/macrophages in bone marrow. Monocyte precursor cells circulate through blood, proliferate and are fused in endosteum to form polykaryocytes. Osteoclasts characteristically contain TRAP (tartrate-resistant acid phosphatase) which is an acid phosphatase having tartrate-resistance and used as a cytochemical marker enzyme to distinguish osteoclasts from other bone tissue cells [Minkin, C., *Calcif. Tissue Int.,* 34:285-290, 1982].

There is variety of causes of periodontal disease. For example, the deposit of dental plaque in periodontal pocket provides a habitat for anaerobic Gram (−) bacteria around, leading to the proliferation of those bacteria deep in periodontal pocket. Toxin of the proliferated anaerobic Gram (−) bacteria and other products thereby might directly destroy the tissues or stimulate immune system. Accordingly, periodontal tissue is destroyed by various related immune responses and inflammation is caused. As a defense mechanism against such inflammation, polymorphonuclear leukocytes and systemic immune response are required. That is, as a result of anaerobic Gram (−) bacteria metabolism, the levels of highly toxic hydrogen sulfide, ammonia and amine are increased in periodontal tissue and at the same time the tissue is destroyed directly by endotoxin such as lipopolysaccharide, a cell wall component, or inflammation in gingiva is developed by extracellular active oxygen, prostaglandin, leukotrien, histamine and interleukin via actions of humoral and cell-mediated immune systems stimulated by such toxins. Bacteria and leukocytes induce the secretion of collagenase, by which collagen, a matrix of periodontal tissue, is decomposed, resulting in recession of gum. If left untreated, it progresses to periodontal disease. Therefore, bactericidal activity and bacteriostatic action against anaerobic Gram (−) bacteria, a fundamental causing factor, elimination of toxins and recovery of damaged periodontal tissue are key points for prevention and treatment of periodontal disease.

For treatment of periodontal disease, in addition to emphasizing on oral hygiene of a patient, non-surgical or surgical scaling, root planing, curettage and periodontal tissue regeneration using new attachment have been performed. However, these surgical treatments are limited to the treatment of progressed diseases only, not effective for prevention of disease, and ask patients to visit a dental clinic necessarily. Most periodontal diseases progress to chronic diseases without early treatment. Supplementary treatment such as administration of antibiotics and local slow-releasing agents has been performed with the fundamental treatment, but it has problems of side effects caused by medicine administered to whole body, which means untargeted areas are also affected, and generating periodontal disease bacteria having a resistance against antibiotics (in fact, periodontal disease bacteria showing antibiotics resistance have been isolated).

To overcome the limited application of surgical treatments and side effects of antibiotics, a novel agent having activity of recovering destroyed and lost periodontal tissue is required for prevention and treatment of periodontal disease.

According to Melcher, an origin of a cell involved in regeneration of periodontal tissue is a key factor affecting the regeneration. For example, if a cell originated from bone is involved, synostosis occurs. If connective tissue originated cells (Ex. gingival fibroblasts) are involved, dental root resorption occurs. If epithelial tissue derived cells are involved, long epithelial attachment is generated, suggesting that regeneration of periodontal tissue is unsatisfactory. If periodontal ligament cell derived cells are involved, most desirable regeneration of periodontal tissue is expected.

Based on the fact that activation of CD4+ T cells inducing secretion of inflammatory cytokines (TNF-, IFN-, GM-CSF, IL-2, IL-6) stimulates the expression of osteoprotegerin ligand on the surfaces of osteoblasts to cause osteoclastogenesis which plays a crucial role in bone destruction, the present inventors fully accept the necessity to develop a new agent having activities of preventing alveolar bone from destruction by suppressing inflammation caused by cytokine secretion, enhancing the proliferation and differentiation of osteoblasts and reducing formation and activation of osteoclasts to protect alveolar bone but not affecting the proliferation of gingival fibroblasts and periodontal ligament cells [Kong, Y. Y. et al., *Nature* 402:304-309, 1999].

Thus, it is confirmed that the best way to promote regeneration of periodontal tissue is to promote the growth of periodontal ligament cells and to maintain the normal growth of gingival fibroblasts. If it is not possible to satisfy the above two conditions, it is preferred for an agent at least not to affect the growths of the two types of cells, especially with preventing soft tissue alternative healing by gingival fibroblast proliferation.

Therefore, the present inventors have studied on herbal medicines to examine the possibility of being an agent to inhibit cytokine secretion, promote the proliferation and differentiation of osteoblasts, and reduce formation and activation of osteoclasts to protect alveolar bone from being destroyed. As a result, the present inventors completed this invention by confirming that a herbal mixture extract of *Pleurotus eryngii, Acanthopanacis Cortex* and *Notoginseng Radix* can inhibit inflammation carried by periodontal disease but not affect the normal growths of gingival fibroblasts and periodontal ligament cells, so that the extract can be effectively used for prevention and treatment of periodontal disease.

DISCLOSURE

Technical Problem

It is an object of the present invention to provide a herbal mixture extract of *Pleurotus eryngii, Acanthopanacis Cortex* and *Notoginseng Radix*. It is another object of the present invention to provide a composition for prevention and treatment of periodontal disease containing the herbal mixture extract as an active ingredient.

Technical Solution

The present invention provides a herbal mixture extract of *Pleurotus eryngii, Acanthopanacis Cortex* and *Notoginseng Radix*.

The present invention also provides a composition for prevention and treatment of periodontal disease containing the herbal mixture extract as an active ingredient.

DESCRIPTION OF DRAWINGS

The application of the preferred embodiments of the present invention is best understood with reference to the accompanying drawings, wherein.

BEST MODE

Figure 1:
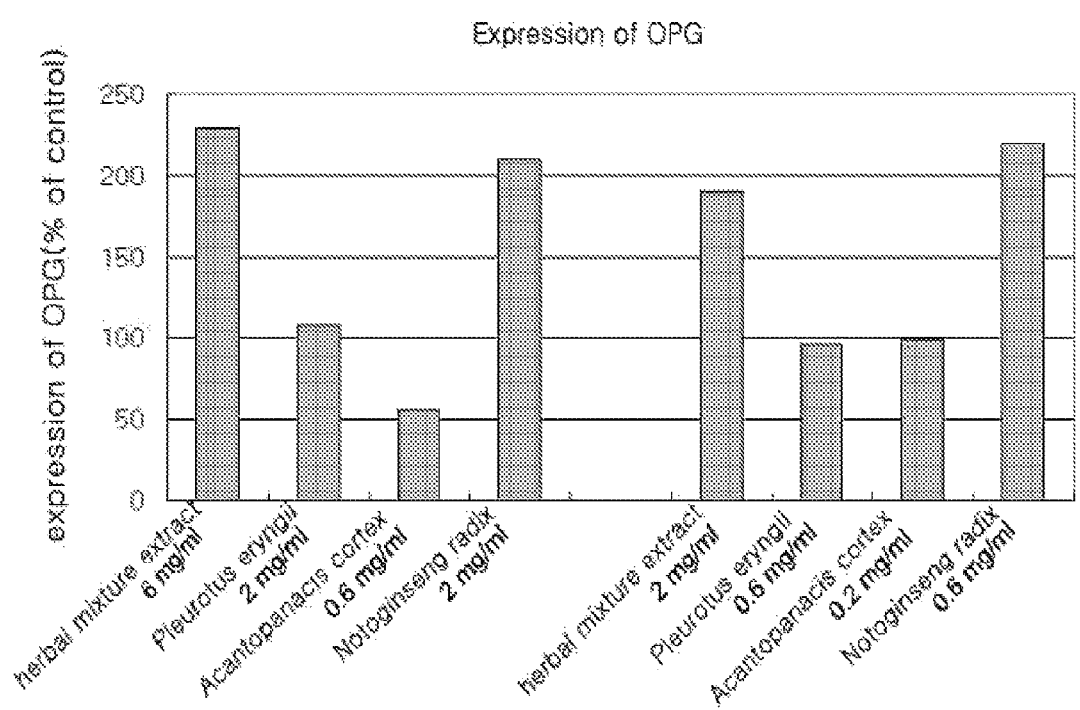
FIG. 1 is a graph showing the effects of herbal mixture extract and each independent extract of the present invention on the osteoprotegerin (OPG) expression in gingival fibroblasts according to an embodiment example of the invention.

Hereinafter, the present invention is described in detail.

The present invention provides a herbal mixture extract of *Pleurotus eryngii, Acanthopanacis Cortex* and *Notoginseng Radix*.

*Pleurotus eryngii*, a kind of saprophyte, belongs to Genus *Pleurotus*, Species *Pleurotus ostreatus* and inhabits the grasslands of the subtropical regions. *Pleurotus eryngii* has been called as Boletus of the steppes or King oyster mushroom in Europe. According to Dongeuibogam, a classical medical literature in Korea, *Pleurotus eryngii* has sweet taste but no toxicity and gives off strong aroma. It helps the functions of stomach and intestines and promotes energy circulation so that *Pleurotus eryngii* has been used as a herbal medicine for the symptoms of benumbed hands and feet, exhaustion and cold knee and back. The components of *Pleurotus eryngii* have not been completely identified, although its characteristics and properties as an alkaline food lowering the level of cholesterol and having an anti-cancer activity have been reported. *Pleurotus eryngii* contains plenty of protein and vitamin, collapse syndrome and has pharmaceutical effect on tonsillitis, mastitis, and various adult diseases. In particular, as an alkaline food, *Pleurotus eryngii* is favored as health food having anti-cancer effect in Japan.

*Acanthopanacis Cortex* is a shrub belonging to Araliaceae, which is only found in far-east Asia in northern hemisphere. In particular, *Acanthopanacis Cortex* is classified as a reserved wild plant in South Korea, which is on the brink of extinction. *Acanthopanacis Cortex* is divided into *Acanthopanax senticosus, Acanthopanax* and *Acanthopanax koreanum*. The roots and barks of *Acanthopanacis Cortex* have been used as top-ranked medicine since they have not shown any toxicity or side effects so far. The leaf of *Acanthopanacis Cortex* contains chiisanoside, which has pharmacological effect. The roots of *Acanthopanacis Cortex* contain not only *Acanthopanacis Cortex* glycoside but also syringin and coumarin glycosides. *Acanthopanacis Cortex* contains acanthosides B and D, which are *Acanthopanacis Cortex* glycosides, and water-soluble polysaccharides enhancing immunity. Its' taste is bitter and hot and it has a property of warming things up. It is known to eliminate gout in liver and nervous systems, invigorate and bring essence in a body. It has been prescribed for such diseases as Oro (fatigue caused by the weakness of five internal organs), Chilsang (seven representative symptoms shown in men caused by the weakness of a body) and difficulty in moving legs. Long-term administration of *Acanthopanacis Cortex* increases energy, protects the stomach, invigorates, clears mind, increases will power, prevents aging, helps having a light heart and clear the blood in a body. So, *Acanthopanacis Cortex* has been used for the treatment of such symptoms as pain in backbone, male impotence, scrotal eczema, female amenorrhea, etc.

*Notoginseng radix* (*Panax notoginseng* (Burk.) F. H. Chen) is a root of a perennial herb belonging to Araliaceae. It is smaller than a ginseng and has 7 pieces of leaves. Its' root is in a small thread drum shape and it is raised widely in Yunnan and Sichuan, southern China. Since the plant has 7 leaves on three branches, it has been called 'Samchil (three-seven)' and often called 'Samchil ginseng' owing to its similar appearance to Korean ginseng. The root has 3~8% saponin and its' major components are ginsenoside $Rb_1$, $Rg_1$, and Re, and notoginsenoside $R_1$, $R_2$, Fa and Fc but small amount of ginsenoside $R_2$, $b_2$, d, e, c are also included. $R_0$ is not contained or if it is, it must be least. Essential oil composition is fewer in *Notoginseng radix* than in *Panax ginseng*. *Notoginseng radix* additionally includes oleanolie acid. Its' root has hemostatic and cardiotonic activities. It was confirmed from animal tests that the root has efficacy of increasing blood flow of coronary artery, decreasing oxygen consumption and lowering the levels of lipid and cholesterol in blood. *Notoginseng radix* also has functions of anti-inflammation, analgesia and hemostasis, so that it is very useful for the treatment of not only inflammatory diseases including hepatitis but also bleeding from trauma, cut, etc., and internal hemorrhage. Applying to a wound or oral administration give the same effects.

The herbal mixture extract of the present invention is prepared by mixing *Pleurotus eryngii, Acanthopanacis Cortex* and *Notoginseng Radix* and then performing extraction using water, $C_1$~$C_4$ alcohol or a mixture thereof. Herein, the alcohol is preferably ethanol. The herbal mixture is composed of 25~55 weight part of *Pleurotus eryngi* 1~20 weight part of Acanthopanacis Cortex and 35~75 weight part of *Notoginseng Radix*, more preferably 35~45 weight part of *Pleurotus eryngii*, 5~15 weight part of *Acanthopanacis Cortex* and 45~55 weight part of *Notoginseng Radix*, and most preferably 40 weight part of *Pleurotus eryngii*, 10 weight part of Acanthopanacis Cortex and 50 weight part of *Notoginseng Radix* Extraction can be performed by the conventional methods such as maceration, infusion and heat extraction by using a proper solvent, and in particular ethanol extraction at 70~80° C. for 3~5 hours is preferred.

The preparation of the herbal mixture extract of the present invention is described in more detail hereinafter.

After eliminating impurities, *Pleurotus eryngii, Acanthopanacis Cortex* and *Notoginseng Radix* are pulverized and mixed, which is put in an extraction vessel. Distilled water is added thereto, followed by hot water extraction. The extract is cooled down at room temperature, filtered by a filter paper, and concentrated under reduced pressure. More precisely, the concentration is preferably proceeded at 20~40° C. under reduced pressure in vacuum condition.

Figure 2:
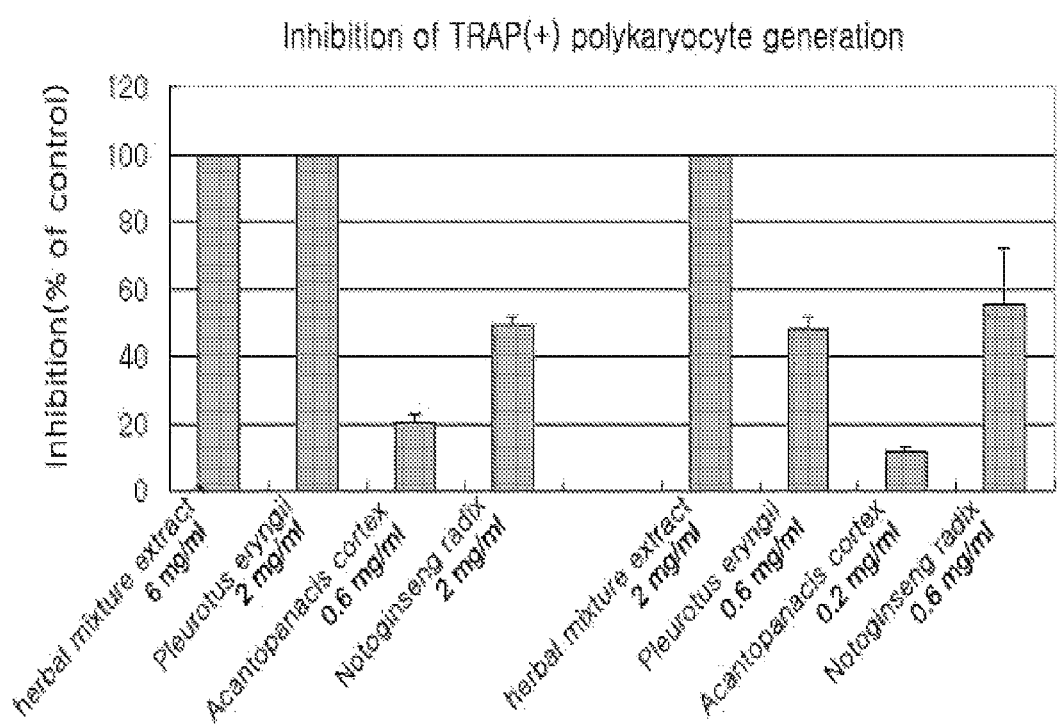
FIG. 2 is a graph showing the effect of herbal mixture extract of the present invention on the formation and activation of osteoclasts according to an embodiment example of the present invention.

The herbal mixture extract of the present invention increases the expression of osteoprotegerin (OPG), thereby inhibits the formation of osteoclasts (FIG. 1). The herbal mixture extract of the present invention reduces the generation of TRAP(+) polykaryocytes, considered as osteoclasts, and the activation of osteoclasts, thereby inhibits bone tissue destruction (FIG. 2).

Figure 3:
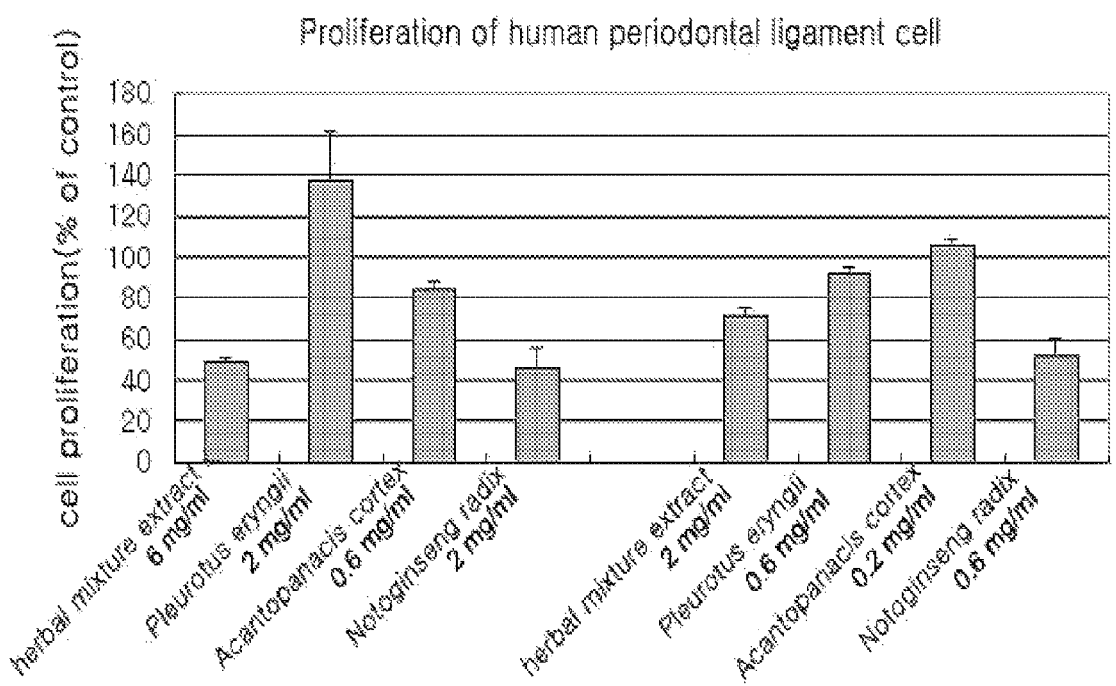
FIG. 3 is a graph showing the effect of herbal mixture extract of the present invention on human periodontal ligament cells according to an embodiment example of the present invention.
Figure 4:
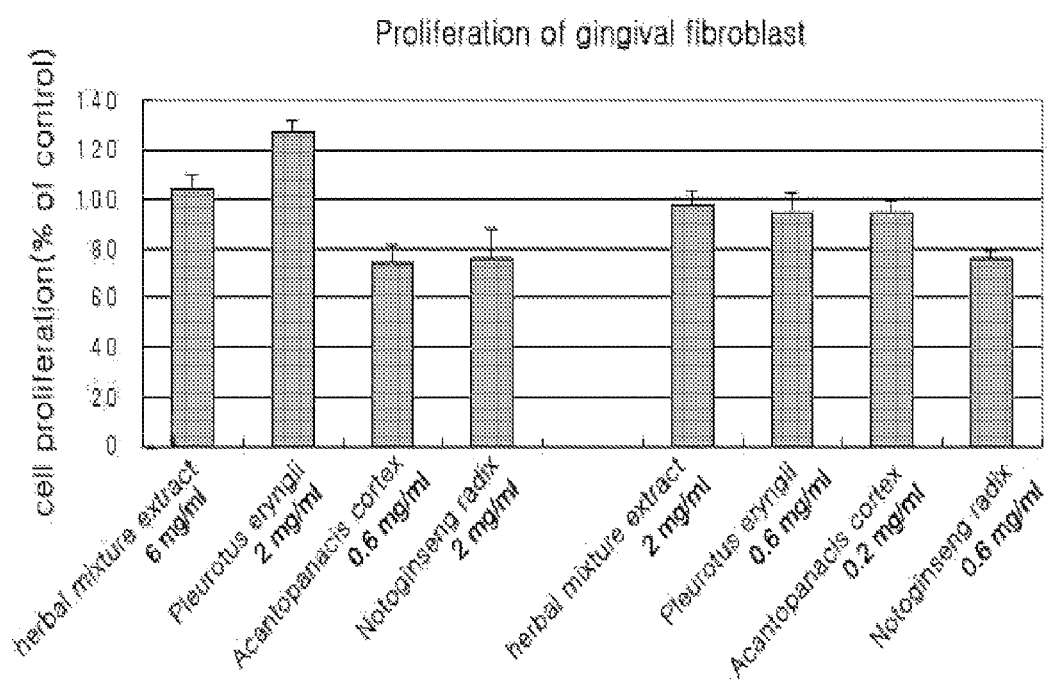
FIG. 4 is a graph showing the effect of herbal mixture extract of the present invention on human gingival fibroblasts according to an embodiment example of the present invention.

The herbal mixture extract of the present invention effectively supports the growth of human periodontal ligament cells and gingival fibroblasts (FIG. 3 and FIG. 4). Therefore, as described above, the herbal mixture extract of the present invention can be effectively used for prevention and treatment of periodontal disease, as medicinal or health food product, because the extract has little toxicity, increases OPG expression in osteoblasts, inhibits formation and activation of osteoclasts to protect alveolar bone from being destroyed and supports the growth of human periodontal ligament cells and gingival fibroblasts.

The present invention also provides a composition for prevention and treatment of periodontal disease containing a herbal mixture extract of *Pleurotus eryngii, Acathopanacis Cortex* and *Notoginseng Radix* as an active ingredient. The composition of the present invention can contain one or more active ingredients showing the same or similar functions to the herbal mixture extract of the invention.

The composition of the present invention can additionally contain one or more active ingredients to supplement the functions of the herbal mixture extract of the invention.

The composition of the present invention contains a preventive and therapeutic composition for periodontal disease containing the herbal mixture extract of the invention as an active ingredient.

The composition of the present invention can also include, in addition to the above-mentioned active ingredients, one or more pharmaceutically acceptable carriers for the administration. Pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions, pills, capsules, granules or tablets, diluents, dispersing agents, surfactants, binders and lubricants can be additionally added. The composition of the present invention can further be prepared in suitable forms for each disease or according to ingredients by following a method represented in Remington's Pharmaceutical Science (the newest edition), Mack Publishing Company, Easton Pa. The composition of the present invention can be administered orally or parenterally (for example, intravenous, hypodermic, local or peritoneal injection). The effective dosage of the composition can be determined according to weight, age, gender, health condition, diet, administration frequency, administration method, excretion and severity of a disease. The dosage 0.1~100 mg/kg per day, preferably 0.1~10 mg/kg per day, and more preferably 0.1~3 mg/kg per day base dosage of *Notoginseng Radix* extract. Administration frequency is once a day or preferably a few times a day.

The composition of the present invention can be administered singly or treated along with surgical operation, radiotherapy, hormone therapy, chemotherapy and biological reaction regulator, to prevent and treat periodontal disease.

The composition of the present invention can include an oral composition for prevention and treatment of periodontal disease containing the herbal mixture extract as an active ingredient.

The herbal mixture extract of the present invention has a therapeutic effect on periodontal disease such as gingivitis and periodontitis, alleviates inflammation on the gingiva although it is not an antibiotic substance and makes the gingiva strong to resist bacterial infection, so that the herbal mixture extract can be prepared as a oral composition for prevention and treatment of periodontal disease. The oral composition containing the herbal mixture extract of the present invention can be prepared as general formulations. Particularly, the oral composition can be prepared as toothpaste, oral mouthwash or mouthrinse. The oral composition of the present invention can be formulated by mixing with abrasives, wetting agents, foaming agents, binders, sweetening agents, pH regulators, antiseptics, pharmacologically active constituents, odoriferous substances, bleaching agents, coloring agents, solvents, etc.

The composition of the present invention can include health food composition for relieving periodontal disease containing the herbal mixture extract as an active ingredient.

At this time, the herbal mixture extract of the present invention can be added as it is or after being mixed with other food or ingredients, according to the conventional method. The mixing ratio of active ingredients is determined by the purpose of use (prevention, health or therapeutic treatment). In the case of producing food or beverages containing the herbal mixture extract of the present invention, the extract is preferably added by less than 100 weight part, more preferably less than 50 weight part, to the raw material. However, the content of the extract might be less than the above when it is administered for long-term to improve health conditions but the effective dosage can contain more than the above amount because the extract of the invention is very safe.

There is no limit in applicable food, which is exemplified by meats, sausages, bread, chocolate, candies, snacks, cookies, pizza, ramyun, noodles, dairy products including ice cream, soups, beverages, tea, drinks, alcoholic drinks and vitamin complex, etc., and in fact every health food generally produced are all included. Health beverages containing the composition of the present invention can additionally include various flavors or natural carbohydrates, etc., like other beverages. The natural carbohydrates above can be one of monosaccharide such as glucose and fructose, disaccharides such as maltose and sucrose, polysaccharides such as dextrin and cyclodextrin, and sugar alcohols such as xylitole, sorbitol and erythritol. As a sweetener, either natural sweetener such as thaumatin and stevia extract or artificial sweetener such as saccharin and aspartame can be used. The ratio of natural carbohydrate to the composition of the present invention is preferably 0.1~20 g to 100 ml, more preferably 1~10 g to 100 ml.

In addition to the ingredients mentioned above, the composition of the present invention can include in variety of nutrients, vitamins, electrolytes, flavoring agents, coloring agents, pectic acid and its salts, arginic acid and its salts, organic acid, protective colloidal viscosifiers, pH regulators, stabilizers, antiseptics, glycerin, alcohols, carbonators which used to be added to soda, etc. The composition of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.05~50 weight part per 100 weight part of the composition of the invention.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Preparation of Herbal Extracts

Cultivated *Pleurotus eryngii, Acanthopanacis Cortex* and *Notoginseng Radix* were purchased from a wholesale dried medicinal herb store.

<1-1> Alcohol Crude Extract of Herbal Mixture

Each medicinal herb was cut into 1~2 cm fractions, which were washed with running water to eliminate impurities. The fractionated herbs were pulverized. *Pleurotus eryngii, Acanthopanacis Cortex* and *Notoginseng Radix* were mixed at the ratio of 4:1:5, resulting in a powder mixture. 200 g of the mixed powder was put in a 3 l flask. Heat extraction was performed using 2,000 ml of ethanol at 78.5° C. for 4 hours with stirring at reflux, which was repeated three times. The extracted solution was filtered and concentrated under reduced pressure under 40° C. by using vacuum rotary evaporator, resulting in herbal mixture extract.

<1-2> Water Crude Extract of Herbal Mixture

Extraction was performed by the same manner as described in Example <1-1> except that water was used as a extraction solvent instead of ethanol.

<1-3> Mixed Solvent Crude Extract of Herbal Mixture

Extraction was performed by the same manner as described in Example <1-1> except that a mixed solvent (water:ethanol=25%:75%) was used as a extraction solvent instead of ethanol.

<1-4> Preparation of each Herbal Extract

Each extract of *Pleurotus eryngii, Acanthopanacis Cortex* or *Notoginseng Radix* was prepared by the same manner as described above.

Experimental Example 1

Increase of OPG (osteoprotegerin) Expression in Osteoblasts by Herbal Mixture Extract Following experiments were performed to examine the effect of herbal mixture extract or each independent herb extract prepared in <Example 1> on the expression of osteoprotegerin in osteoblasts.

<1-1> Osteoblast Selection and Cell Culture

The following three types of cells were used to investigate the effect of the herbal mixture extract or each independent herbal extract of the present invention on the proliferation of osteoblasts. A human osteosarcoma derived cell line MG-63 (ATCC No, CRL-1427) and a mouse muscle derived cell line C2C12 (ATCC No. CRL-1772) were distributed from American Type Culture Collection (ATCC, USA). The cells were cultured in DMEM (Gibco, BRL, USA) supplemented with 10% FBS (fetal bovine serum) in a 37° C. 5% $CO_2$ incubator with 100% humidity.

As a primary culture cell, osteoclasts obtained from Sprague-Dawley rat calvaria (RCC) were used. Precisely, frontal bone and parietal bone were extracted from calvaria of Sprague-Dawley rat at 19 days of age, and then treated with an enzyme solution containing 0.1% collagenase, 0.05% trypsin and 0.5 mM EDTA, serially at 37° C. for 10 minutes, 10 minutes, 10 minutes, 20 minutes and 20 minutes, respectively. Types I~V cells were separated. Among them, types IV and V cells, composed mainly of those having characteristics of osteoblasts, were mixed and primary cultured in DMEM supplemented with 10% FBS. Cells were collected using trypsin-EDTA solution and counted for further use in experiments.

<1-2> Expression of OPG (Osteoprotegerin) Inhibiting the Generation of Osteoclasts MG-63 cell culture medium having approximately at the density of $10^6$ cells/20 ml was removed from 100 mm cell culture dish. The dish was washed with 5 ml of DPBS (Dulbeco's modified phosphate buffered saline). The buffer was removed and 0.5 ml of trypsin-EDTA was spread on the culture dish, which stood in a $CO_2$ incubator for one minute to take the cells off. The cells were put in 5 ml of DMEM supplemented with 10% FBS and mixed well. The solution was put in a 15 ml test tube, followed by centrifugation at 1500 rpm for 5 minutes. Upon completion of centrifugation, supernatant was removed and the remaining cell culture solution was transferred into 5 ml of DMEM supplemented with 10% FBS and mixed well. The numbers of cells were counted by haemacytometer and then distributed into a 96-well plate at the concentration of $10^4$ cells/well. 24 hours after distribution, herbal extract diluted in DMEM containing penicillin/streptomycin at different concentrations of 0.22, 0.66, 2 and 6 mg/ml, was treated to cells.

To increase reliability of the test results, positive control was treated with 20 mM $CaCl_2$ to induce 2~5 fold higher expression of OPG than in negative control. 24 hours after the treatment, each supernatant was diluted (1/200) using DPBS. 100 μl of the diluted solution was put in ELISA plate for further analysis. OPG ELISA kit (OCT) was used and optical density was measured at 450 nM. The level of OPG in the extract-treating group was converted as relative % to that in extract-non-treating control group using standard curve, according to the below Mathematical Formula 1.

OPG expression rate (%)=(1−O.D.$_{450}$ of experimental group/O.D.$_{450}$ of control group)×100  <Mathematical Formula 1>

(In the Formula, O.D.$_{450}$ Means Optical Density at 450 Nm)

From the result of investigation on the expression of OPG, an inhibitor of the generation of osteoclasts, it was confirmed that the herbal mixture extract of the present invention increases the expression of OPG dose-dependently, and maximum OPG expression (up to 230%) was observed at the concentration of 6 mg/ml. And the herbal mixture extract promotes the expression of OPG better than each independent herbal extract (FIG. 1).

Experimental Example 2

Inhibition of Osteoclast Proliferation by Herbal Mixture Extract

To examine whether the herbal mixture extract of the present invention and each independent herbal extract could inhibit the formation of osteoclasts and reduce cellular activity, the present inventors performed following experiments.

<2-1> Isolation of Osteoclast Precursor Cells and Differentiation of Osteoclast Precursor Cells into Mature Osteoclasts To isolate mouse bone marrow cells, male mouse at 7-9 weeks old was sacrificed by kinked neck, then femur and tibia were extracted under aseptic condition. Soft tissue was eliminated and both ends of ilium were cut out. 1 ml of an enzyme solution containing 0.1% collagenase (Gibco), 0.05% trypsin and 0.5 mM EDTA (Gibco) was injected into one end of medullary cavity by using 26 G needle. Bone marrow was taken out, followed by stirring for 30 minutes. Bone marrow cells were recovered and pre-cultured for 24 hours in α-MEM (α-minimum essential medium) supplemented with 10% FBS. Unattached cells were obtained. The unattached cells, osteoclast precursor cells, were inoculated into a plate ($2 \times 10^5$ cells per well), followed by culture. The herbal mixture extract of the invention was treated to α-MEM containing 20 ng/ml of macrophage-colony stimulating factor (M-CSF, Peprotech, USA) and 30 ng/ml of receptor activator of nuclear factor-B ligand (RANKL, Peprotech, USA) during the 8-day of culture. Upon completion of the culture, cells were fixed and TRAP staining was performed to examine the generation of osteoclasts. To further examine the activity of osteoclasts, resorption areas of taken-off cells were investigated.

<2-2> Inhibition of TRAP(+) Polykaryocyte Generation

Upon completion of the bone marrow cell culture, attached cells were washed with PBS and fixed with citrate-acetate-formaldehyde for 5 minutes. The cells were further cultured in 37° C. acetate buffer (pH 5.0) containing naphthol AS-BI phosphate, fast Garnet GBC solution and 7 mM tartrate buffer (pH 5) for one hour, followed by staining with TRAP. TRAP (+) polykaryocytes having more than 3 nuclei were considered as osteoclasts.

In the present invention, bone marrow, known to contain osteoclast precursor cells, was used to induce the differentiation of osteoclasts, and TRAP(+) polykaryocytes were considered as osteoclasts. Osteoclast precursor cells were treated with the herbal mixture extract or each independent herbal extract of the present invention prepared in Example 1, followed by culture for 8 days. Then, the numbers of TRAP(+) polykaryocytes were measured and thereby inhibition rate was calculated according to the below Mathematical Formula 2. The activity of TRAP, an osteoclast marker enzyme, was also measured. As a result, formation of TRAP(+) polykaryocytes was inhibited up to 100% in herbal mixture extract-treating group, compared with extract-non-treating control. The above results indicate that the herbal mixture extract of the present invention has inhibiting effect on the formation of osteoclasts (FIG. 2).

TRAP(+)polykaryocyte generation inhibiting rate (%)=100−[(Number of polykaryocytes of experimental group/Number of polykaryocytes of control group)×100]  <Mathematical Formula 2>

Experimental Example 3

Effect of Herbal Mixture Extract of the Invention on the Proliferations of Gingival Fibroblasts and Periodontal Ligament Cells Following experiments were performed to investigate the effect of the herbal mixture extract or each independent herbal extract of <Example 1> on the proliferations of human periodontal ligament cells and gingival fibroblasts.

<3-1> Selection of Human Periodontal Ligament Cells and Gingival Fibroblasts and Cell Culture Periodontal ligament of premolar teeth extracted from normal healthy man with the purpose of orthodontic management was scratched by curette under the aseptic condition, which was then placed on a culture dish. Small amount of DMEM (Gibco, BRL, USA) supplemented with 10% FBS (fetal bovine serum) was added thereto, followed by culture. A part of gingiva was also taken off to obtain gingival fibroblasts, which was cultured by the same manner as described above. By observation under microscope, it was confirmed that cells were explanted from the tissues. After colony was formed, each tissue sample was eliminated and cell growth in a single layer was induced, followed by subculture.

<3-2> Proliferations of Human Periodontal Ligament Cells and Gingival Fibroblasts Human periodontal ligament cells and gingival fibroblasts were distributed in a 24-well plate at the concentration of 20,000 cells/well, followed by culture for 48 hours in a 5% $CO_2$ incubator. Then, the herbal mixture extract and each independent herbal extract, contained in a culture medium at different concentrations, were treated, followed by further culture for 48 more hours. After eliminating the culture medium, trypsin-EDTA was added thereto. The numbers of cells were measured by hemacytometer. The proliferation rate was measured by comparing the proliferation of a control which was not treated with any extract, by the below Mathematical Formula 3. The proliferations of gingival fibroblasts and periodontal ligament cells were rather normally maintained in herbal mixture extract-treating group than in groups each treated with independent herbal extract (FIG. 3 and FIG. 4).

Cell proliferation rate(%)=Number of cells of experimental group/Number of cells of control group× 100  <Mathematical Formula 3>

Each component of the herbal mixture extract of the present invention does not display any of the above mentioned properties, but when they are mixed (as herbal mixture extract), the mixture displays desirable properties to maintain normal proliferation of gingival fibroblasts and periodontal ligament cells.

The Manufacturing Examples of the composition for the present invention are described hereinafter.

Manufacturing Example 1

Preparation of Pharmaceutical Formulations

<1-1> Preparation of Powders

| | |
|---|---|
| Herbal mixture extract | 2 g |
| Lactose | 1 g |

Powders were prepared by mixing all the above components and filled airtight bag with them.

<1-2> Preparation of Tablets

| | |
|---|---|
| Herbal mixture extract | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Herbal mixture extract | 100 mg |
| Corn starch | 100 mg |
| Lactose | 100 mg |
| Magnesium stearate | 2 mg |

Manufacturing Example 2

Preparation of Mouthwash Gargle

| | |
|---|---|
| Herbal mixture extract of the present invention | 0.01~1.0 g |
| xylitole | 5~10 g |
| Ethyl alcohol | 5~15 g |
| Sorbitol | 5~15 g |
| Sodium saccharin | 10~100 mg |
| Sodium monofluorophosphate | 500~1000 mg |
| Sodium lauryl sulfate | 100~200 mg |
| Polysorbate 20 | 100~1000 mg |
| Peppermint flavor | 10~100 mg |
| Sodium benzoate | 10~100 g |
| Purified water | Proper amount |
| Color | Proper amount |
| Total | 100 g |

An oral composition gargle having preventive and therapeutic effect for periodontitis was prepared by mixing the components above according to the conventional method for mouthwash gargle.

Manufacturing Example 3

Preparation of Food

Foodstuff containing the herbal mixture extract of the present invention was prepared as follows.

<3-1> Preparation of Flour Food

Health improving flour food was prepared by adding the herbal mixture extract of the present invention by 0.5~5.0 weight part to wheat flour and then making the flour into bread, cakes, cookies, crackers and noodles.

<3-2> Preparation of Dairy Products

The herbal mixture extract of the present invention was added by 5~10 weight part to milk to prepare dairy products such as butter, ice cream, etc.

<3-3> Preparation of Sunsik

Brown rice, barley, glutinous rice and *coix* (job's tear) were gelatinized by the conventional method, followed by drying. The dried mixture was distributed and pulverized, resulting in 60-mesh size grain powders.

Black bean, black sesame and *perilla* were steamed and dried by the conventional method. The dried mixture was distributed and pulverized, resulting in 60-mesh size grain powders.

The herbal mixture extract of the present invention was vacuum-concentrated under reduced pressure using a vacuum concentrator, which was then spray-dried with a hot-air drier. The dried material was pulverized by a grinder, resulting in 60-mesh size grain powders.

The prepared grain, seeds, and dried herbal mixture extract powders were all mixed at the following ratio.

Grain (brown rice 30 weight part, *coix* 15 weight part, barley 20 weight part), Seeds (*perilla* 7 weight part, black bean 8 weight part, black sesame 7 weight part), Dried powder of herbal mixture extract (3 weight part),

*Ganoderma lucidum* (0.5 weight part),

*Rehmannia glutinosa* (0.5 weight part)

Manufacturing Example 4

Preparation of Beverages

<4-1> Preparation of Carbonated Beverages

Sugar (5~10%), citric acid (0.05~0.3%), caramel (0.005~0.02%) and vitamin C (0.1~1%) were mixed, to which purified water (79~94%) was added to make syrup. The prepared syrup was sterilized at 85~98° C. for 20~180 seconds, then mixed with cooling water at the ratio of 1:4. Then, carbon dioxide gas (0.5~0.82%) was given to the mixture to prepare carbonated beverages containing the herbal mixture extract of the present invention.

<4-2> Preparation of Health Beverages

Acid fructose (0.5%), oligosaccharide (2%), sugar (2%), salt (0.5%) and water (75%) were all mixed with the herbal mixture extract evenly, followed by sterilization. The mixture was put in a small container such as a glass bottle or pat bottle, resulting in health beverages.

<4-3> Preparation of Vegetable Juice 5 g of the herbal mixture extract of the present invention was added to 1,000 ml of tomato or carrot juice to prepare health vegetable juice.

<4-4> Preparation of Fruit Juice 1 g of the herbal mixture extract of the present invention was added to 1,000 ml of apple or grape juice to produce health fruit juice.

INDUSTRIAL APPLICABILITY

As described hereinbefore, the herbal mixture extract of *Pleurotus eryngii*, *Acanthopanacis Cortex* and *Notoginseng Radix* of the present invention increases the expression of osteoprotegerin (OPG) in osteoblasts, inhibits the formation and activation of osteoclasts, inhibits the proliferation of osteoclasts eventually and supports the proliferation of dental annular ligament cells and gingival fibroblasts. Therefore, the herbal mixture extract of the present invention can be effectively used for the prevention and treatment of periodontal disease including gingivitis and periodontitis as a medicinal or health food product.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for treating periodontal disease in a mammal in need thereof comprising orally or parenterally administering a therapeutically effective amount of an extract of a mixture of *Pleurotus eryngii*, *Acanthopanacis Cortex* and *Notoginseng Radix* to the mammal in need thereof, wherein the extract is composed of 25-45 weight part of *Pleurotus eryngii*, 1-20 weight part of *Acanthopanacis Cortex* and 35-65 weight part of *Notoginseng Radix* and the extract is prepared by using a solvent of water, ethanol or a mixture thereof.

2. The method according to claim 1, wherein the extract is composed of 35-45 weight part of *Pleurotus eryngii*, 5-15 weight part of *Acanthopanacis Cortex* and 45-55 weight part of *Notoginseng Radix*.

3. The method according to claim 1, wherein the extract is composed of 40 weight part of *Pleurotus eryngii*, 10 weight part of *Acanthopanacis Cortex* and 50 weight part of *Notoginseng Radix*.

4. The method according to claim 1, wherein the periodontal disease is gingivitis or peridontitis.

5. The method according to claim 1, wherein the extract accelerates osteoprotegerin expression in osteoblasts.

6. The method according to claim 1, wherein the extract inhibits osteoclast proliferation.

7. The method according to claim 1, wherein the extract is prepared at 70-80° C. for 3-5 hours.

8. The method according to claim 1, wherein the extract is administered as a health food product.

* * * * *